(12) United States Patent
Watson

(10) Patent No.: US 7,025,723 B1
(45) Date of Patent: *Apr. 11, 2006

(54) BELTLESS FIBER OPTIC LABOR CONTRACTION SENSING DEVICE

(76) Inventor: Richard L. Watson, 1985 Cougar Trail, McPherson, KS (US) 57465

(*) Notice: Subject to any disclaimer, the term of this patent is extended or adjusted under 35 U.S.C. 154(b) by 0 days.

This patent is subject to a terminal disclaimer.

(21) Appl. No.: 10/642,432

(22) Filed: Aug. 15, 2003

Related U.S. Application Data

(63) Continuation of application No. 09/757,733, filed on Jan. 10, 2001, now Pat. No. 6,607,486.

(60) Provisional application No. 60/175,356, filed on Jan. 10, 2000.

(51) Int. Cl.
*A61B 5/00* (2006.01)

(52) U.S. Cl. .................. 600/304; 600/588; 600/591; 73/800; 250/217.14

(58) Field of Classification Search .............. 600/304, 600/551, 588, 591, 587; 73/800; 250/217.14, 250/217.16, 217.18, 227.14, 227.16, 227.18
See application file for complete search history.

(56) References Cited

U.S. PATENT DOCUMENTS

| | | |
|---|---|---|
| 3,913,563 A | 10/1975 | Ball |
| 4,408,495 A | 10/1983 | Couch et al. |
| 4,542,291 A | 9/1985 | Zimmerman |
| 4,947,853 A | 8/1990 | Hon |
| 5,042,503 A | 8/1991 | Torok et al. |
| 5,070,888 A | 12/1991 | Hon et al. |
| 5,118,931 A | 6/1992 | Udd et al. |
| 5,134,281 A | 7/1992 | Bryenton et al. |
| 5,182,449 A | 1/1993 | Johnson et al. |
| 5,218,972 A | 6/1993 | Gorsuch et al. |
| 5,224,490 A | 7/1993 | Allen et al. |
| 5,265,475 A | 11/1993 | Messinger et al. |
| 5,425,775 A | 6/1995 | Kovacevic et al. |
| 5,436,444 A | 7/1995 | Rawson |
| 5,882,300 A | 3/1999 | Malinouskas et al. |
| 5,935,061 A | 8/1999 | Acker et al. |
| 6,110,130 A | 8/2000 | Kramer |
| 6,381,482 B1 * | 4/2002 | Jayaraman et al. ......... 600/388 |

\* cited by examiner

*Primary Examiner*—Robert L. Nasser

(57) ABSTRACT

A beltless fiber optic labor contraction sensing device including a fiber optic strain sensor for detecting labor contractions during childbirth. The fiber optic strain sensor includes an optic cable, a light source for transmitting a light beam through the optic cable and a light detector for identifying changes in the optical signal. The fiber optic strain sensor is operable to generate an appropriate response to any changes in the optical signal that are caused by the application of force against the fiber optic cable. An adhesive pad or sensor jacket is provided to secure the fiber optic strain sensor to the mother's abdomen without the use of a belt or strap. The contraction device includes wireless communication for transmitting an output signal to a standard contraction recording device. Further, one or more of the components of the labor contraction sensing device are fabricated so as to be disposable.

6 Claims, 3 Drawing Sheets

BELTLESS FIBER OPTIC LABOR CONTRACTION SENSING DEVICE

This U.S. patent application is a continuation of U.S. application Ser. No. 09/757,733, filed Jan. 10, 2001 now U.S. Pat. No. 6,607,486, which claims priority to U.S. Provisional Patent Application No. 60/175,356, filed on Jan. 10, 2000.

FIELD OF THE INVENTION

The present invention relates to a device for monitoring labor contractions during childbirth. Particularly, the present invention relates to a fiber optic labor contraction sensor adapted to adhere to a females abdomen without the use of a belt or strap. More particularly, the beltless fiber optic labor contraction sensor includes a fiber optic strain sensor that generates an output signal in response to labor contractions and communicates the output signal to a signal transceiver. The signal transceiver is operable to communicate the incidence of labor contractions through radiotelemetry or other wire less communication.

BACKGROUND OF THE INVENTION

During childbirth, both the strength and frequency of the mother's labor contractions are monitored. To monitor labor contractions, medical personnel typically utilize force-type strain gauges held against the mother's abdomen by an elastic belt placed around the mother's waist. In use, such monitors are, however, bulky and extremely uncomfortable. Further, conventional monitors are generally highly cumbersome and fail to provide the mother with mobility outside the bed during the birthing process. More specifically, a mother is normally restricted to the bed during childbirth and if the mother needs to exit the bed and move about, she must first remove the attached monitor. Another limitation of presently employed monitoring devices is the limited range of mobility afforded the mother due to the signal cables connecting the monitoring device to a contraction recording system.

The problems described above are not intended to be exhaustive but are merely a few of those tending to reduce the effectiveness of the monitors presently used to detect labor contractions. These problems demonstrate that presently used monitors are not satisfactory and illustrate further the need for an improved device for detecting labor contractions.

SUMMARY OF THE INVENTION

In accordance with the present invention, a labor contraction sensing device includes a fiber optic strain sensor that is adhered to the mother's abdomen for detecting the strength and frequency of labor contractions during childbirth. The fiber optic strain sensor is in signal communication with a signal transceiver having a signal transmitter that is in wire less communication with a standard contraction recording device or other monitoring equipment.

Therefore, in accordance with a general embodiment of the present invention, there is provided a fiber optic strain sensor including at least one fiber optic cable having first and second ends. A light source is located at one end of the fiber optic cable for transmitting a light beam through the fiber optic cable to the opposite end of the fiber optic cable. A light detector is located at the opposite end of the cable for detecting fluctuations in the transmitted fiber optic light beam. In operation, any external forces acting against the fiber optic cable, such as the tightening of the mother's abdomen due to the onset of a contraction, results in changes in the optical signal of the transmitted light beam. These fluctuations are detected by the light detector and an appropriate output signal is generated by optical signal processing electronics. The sensor output signal is communicated to a signal transceiver, which includes a signal receiver and transmitter.

In a further embodiment, the signal transmitter is a radio transmitter. Utilizing a radio transmitter as the signal transmitter provides the user with wire less communication between the labor contraction sensing device and a standard contraction recording system. Additionally, the fiber optic strain sensor is specially designed to be adhered to the mother's abdomen without the use of a belt. Specifically, the fiber optic strain sensor includes an adhesive surface or is placed within an adhesive cover or jacket that allows the fiber optic strain sensor to be conveniently and comfortably adhered to the abdomen of the mother. The beltless design together with wireless communication provides a labor contraction sensing device that offers increased mobility to the expecting mother relative to existing contraction sensing devices.

DETAILED DESCRIPTION OF THE PREFERRED EMBODIMENTS

Referring to FIGS. 1 through 5, there is shown embodiments of a labor contraction sensing device (10) of the present invention. Before describing the invention, it should be first understood that the term "fiber optic strain sensor" can refer to any optical detection system utilizing fiber optics, wires, lines, or cables through which a light beam is passed and fluctuations or changes in that light beam caused by the external application of force upon the system are identified as changes in the transmitted optical signal.

Figure 1:
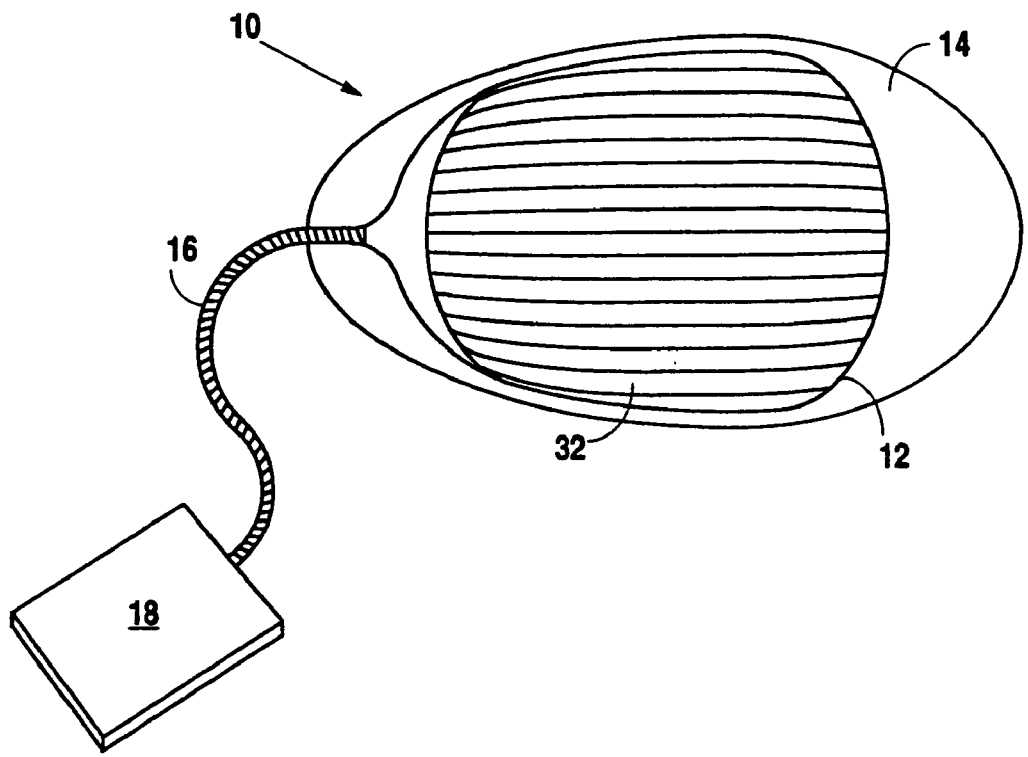
FIG. 1 is a top perspective view of the labor contraction sensing device of the present invention.

As illustrated in FIG. 1, a contraction sensing device (10) embodying the present invention comprises a fiber optic strain sensor (12) having a generally elliptical shape to better conform to the contour of the mother's abdomen. The strain sensor (12) is secured to an adhesive pad (14) that provides removable attachment of the strain sensor (12) to the mother's skin surface (44). As discussed below, a signal line (16) provides communication between the sensor electronics housed in an electrical box (18) and the fiber optic portion of the strain sensor (12). In a preferred embodiment, the electronics box (18) houses a wireless signal transmitter (28) for transmitting an output signal that corresponds to the labor contractions detected by the strain sensor (12). In use, the mother's movement is therefore not restricted by one or more communication lines extending between the device

(10) and a standard contraction recording device as are present with standard contraction monitoring systems.

Figure 1A:
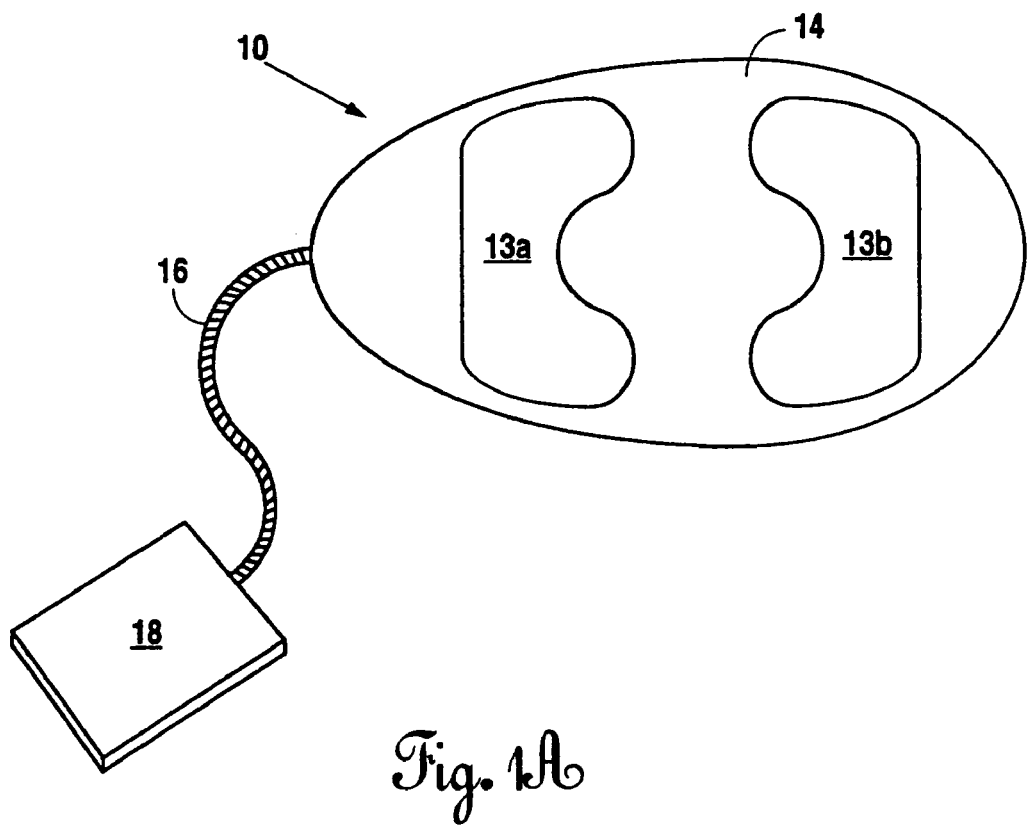
Figure 2:
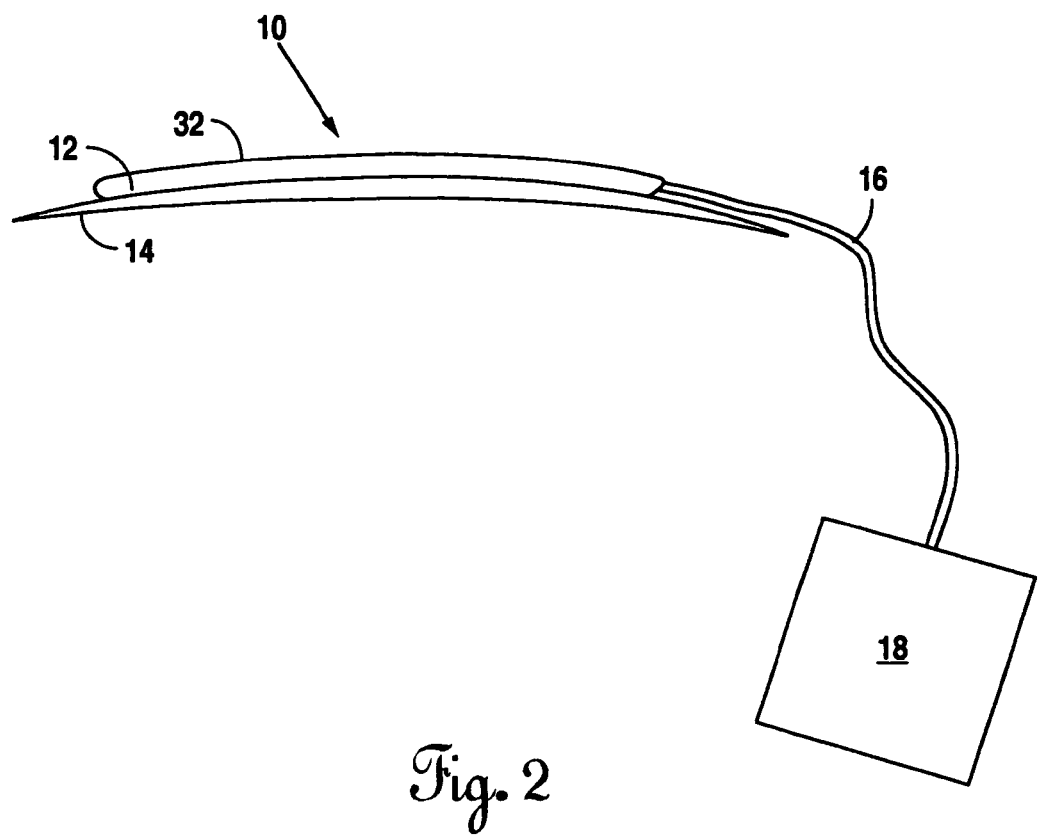
FIG. 2 is a side perspective view of the labor contraction sensing device of the present invention.

Referring to FIG. 2, there is illustrated a side view of the contraction sensing device (10). As shown, the strain sensor (12) and underlying adhesive pad (14) are preferably thin. Such narrow design is not bulky or cumbersome, and thus, reduces user discomfort associated with traditional contraction monitoring systems. Though the preferred embodiment is designed to be narrow in thickness, multiple surface shapes and configurations can be used without deviating from the scope of the present invention. For instance, the sensing device (10) can have rectangular or circular surfaces. Alternatively, as shown in FIG. 1A, the sensing device (10) can be fabricated with different surface portions (13a and 13b) having alternate shapes for conforming to varying contours of the abdominal surface. It is preferable, however, that the strain sensor be fabricated as narrow as possible to maximize user comfort.

Referring to FIGS. 1 and 2, a signal line (16) provides communication between the strain sensor (12) and the electronics box (18). Within the electronics box (18) is framed the components necessary to inject a light beam through the fiber optic cable (20) of the strain sensor (12), which is preferably located within signal line (16), and to detect any fluctuations in the optical signal. Such components include a light source, light detector and optical signal processing electronics. A preferred embodiment includes a wire less signal transmitter (28) operable to communicate with a contraction recording device. Such contraction recording devices are well known in the art and one skilled in the art would readily know how to place the recording device in wireless communication with the signal transmitter.

Figure 3:
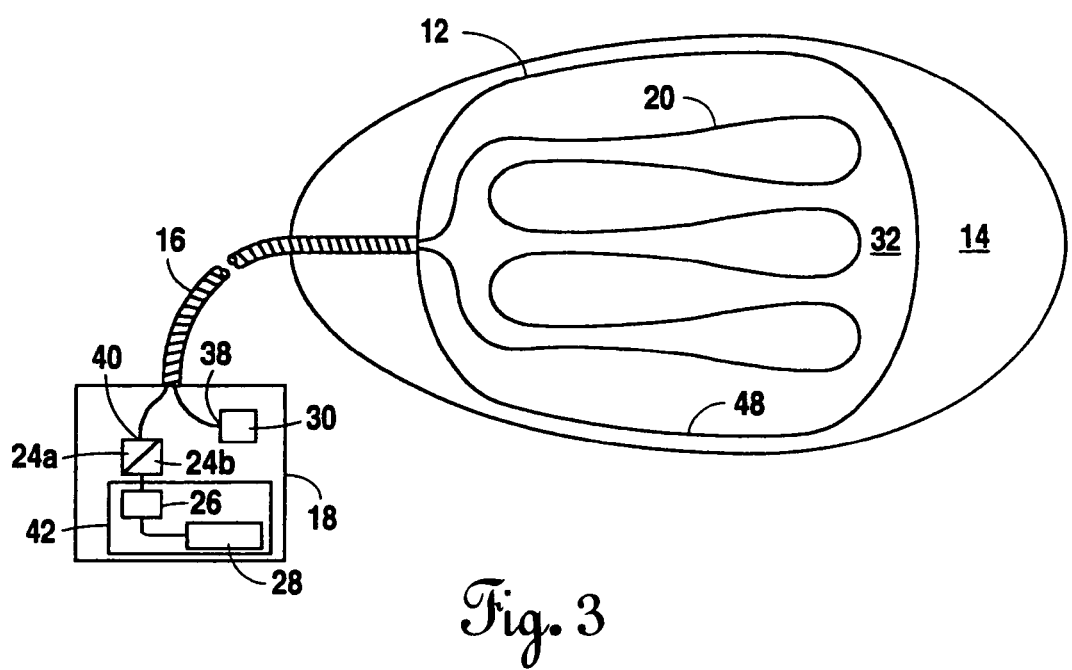
FIG. 3 is a cross sectional view of the labor contraction sensing device illustrated in FIG. 1.

As shown in FIG. 3, the preferred strain sensor (12) includes a fiber optic cable (20) embedded within a sensor cover (32). In another embodiment (not shown), some or all of the electronic components, including a light source, light detector, optical signal processing electronics and power supply may be embedded within the sensor cover (32). The sensor cover (32) is preferably fabricated from soft flexible plastic; however, any other material that is flexibly responsive to labor induced changes in the surface contour of the mother's abdomen can be used. For instance, materials suitable for use in the present invention include rubber, fabric, nylon mesh, or other like materials. As will be appreciated from further descriptions of the alternative embodiments described herein, the fiber optic sensor (12) may be held against the skin surface (44) by a conventional drape (not shown). More particularly, the drape is shaped to overly the sensor (12) and the perimeter of the drape is adapted to engage the skin surface (44) so that the sensor (12) is held firmly against the skin surface (44).

Figure 4:
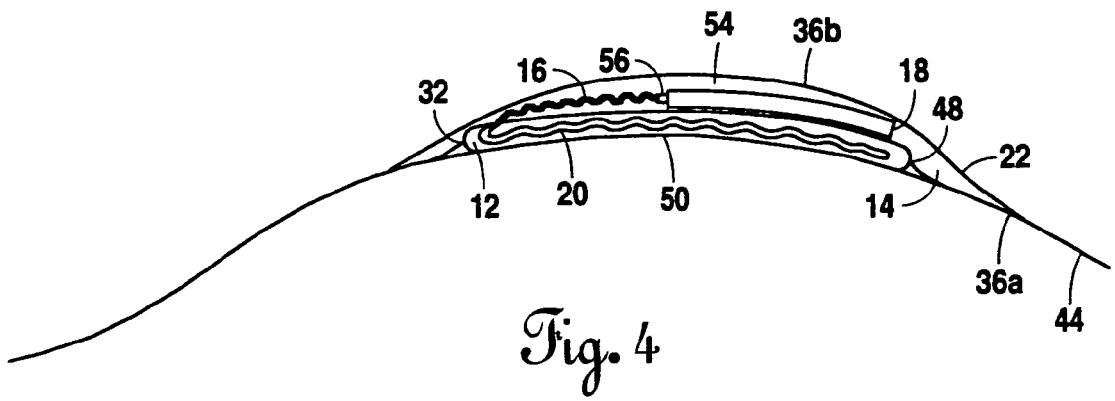
FIG. 4 is a cross sectional view of a preferred embodiment of the labor contraction sensing device of the present invention.

As illustrated in FIG. 4, a preferred embodiment of the present invention provides unitary fabrication of the strain sensor (12) and adhesive pad (14). Particularly, the adhesive pad (14) and sensor (12) are made as a single component for more cost effective fabrication and convenient disposal following use. As shown, a preferred adhesive pad (14) includes a lower adhesive surface (36a) and upper cover surface (36b). The upper and lower surfaces (36a–b) of the adhesive pad (14) are joined together to form a sensor jacket (22) defining an interior compartment or pouch (54) for holding the electronics box (18) and any other necessary components. Referring to FIGS. 3 and 4, the inner edge of the lower surface (36a) of the adhesive pad (14) is preferably attached about the outer edge (48) of the sensor cover (32) using commonly known welding or stitching techniques. In embodiments of the present invention, many of the components, including the sensor jacket (22), sensor cover (32) and adhesive pad (14) can be formed from single or multiple layers of a flexible polymer sheet (or drape), or mesh fabric. A suitable material for forming these components is a clear polymer sheet sold under the tradename "TEGADERM" from Minnesota, Mining and Manufacturing Company, which is commonly known as 3M. As the preferred embodiment in FIG. 4 illustrates, adhering the pad lower surface (36a) directly to the mother's skin surface (44) allows the lower surface (50) of the sensor (12) to be positioned substantially adjacent to the mother's skin surface (44). In this embodiment, the sensor lower surface (50) can also have an adhesive surface for providing further attachment to the skin surface (44).

In a further embodiment (not shown), the components housed in the electronics box (18) are embedded together with the fiber optic cable (20) within the sensor cover (32) to form the sensor (12). In use, the senior (12) is positioned against the mother's skin surface (44) and a drape material such as the polymer sheet described above is placed in overlying relation to the sensor (12). The perimeter of the drape material is then adapted to engage the mother's skin surface (44) such that the sensor (12) is held against the mother's abdomen.

Figure 5:
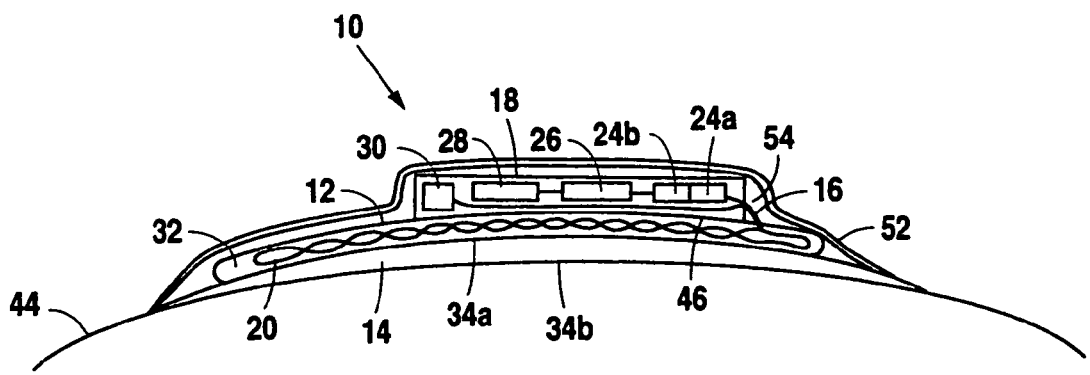
FIG. 5 is a cross sectional view of an alternative embodiment of the labor contraction sensing device of the present invention.

In an alternative embodiment, shown in FIG. 5, the sensor (12) is held within a sensor jacket (22) in overlapping relation to the adhesive pad (14). In this embodiment, the adhesive pad (14) is provided with an upper adhesive surface (34a) for holding the sensor (12) and a lower adhesive surface (34b) for adhering to the mother's skin (44). Providing pad (14) with an upper adhesive surface (34) allows for the removable detachment of the strain sensor (12) from the adhesive pad (14), thereby enabling the user to recycle the strain sensor (12) together with a new adhesive pad (14). It should be understood by those skilled in the art, however, that a variety of sensor (12) and adhesive pad (14) configurations and combinations can be used without deviating from the scope of the present invention. Thus, the sensor (12) and pad (14) can be detachably connected or fabricated as an integral component.

The electronics box (18) is preferably not fabricated as a disposable component. As such, the electronics box (18) can be provided with an adhesive surface (46) for adhering the box (18) to the surface of the sensor cover (32), or alternatively, for adhering the electronics box (18) directly to the mother's skin surface (44). Referring to FIG. 4, the electronics box (18) can be releasably positioned within the pouch (54) of the sensor jacket (22). In this way, the user of the device (10) simply inserts the electronic box (18) into the jacket pouch (54) and plugs the signal line (16) into a socket (56) to connect the fiber optic cable (20) with the electronics box (18), which houses the light source (30), light detector (24) and signal transceiver (42). As shown in FIG. 3, the box (18) is provided as a component apart from the sensor (12). In either embodiment shown in FIGS. 3 and 4, however, the electronics box (18) can be readily unplugged from the fiber optic cable (20) or signal line (16) and the used sensor (12), pad (14) and/or jacket (22) properly disposed of. Though it is envisioned that the electronics box (18) is fabricated as a separate component, the electronics could be provided as an integral component of the device (10) without deviating from the scope of the present invention.

Referring to FIG. 3, the strain sensor (12) comprises a fiber optic cable or other optical transmission line (20) embedded within a sensor cover (32). The fiber optic cable (20) has a first end (38) and a second end (40). The fiber optic cable (20) can be any typical fiber optic cable or other optical transmission line known to those skilled in the art. A light source (30) is positioned adjacent to the first end (38) for transmitting a light beam or optical signal through the fiber optic cable (20). Positioned adjacent to the second end (40) of the fiber optic cable (20) is a light detector (24a) and signal decoder (24b) for monitoring variations in the optical signal as it passes through the fiber optic cable (20). In this way, the light source (30) transmits a light beam through the fiber optic cable (20) and any external applications of force against the cable (20), such as the force of a labor contraction, results in fluctuations in the optical signal that are identified by the light detector (24a) as changes in the optical signal. A signal decoder (24b) is operable to decode the identified optical signal and generate an appropriate response, such as an electrical output signal, that is transmitted to a signal transceiver (42).

In the preferred embodiment, the signal transceiver (42) comprises a signal receiver (26) in communication with a signal transmitter (28). The signal receiver (26) is operable to transmit the output signal received from the signal decoder (24b) to the signal transmitter (28). In its preferred embodiment, the signal transmitter (28) is a radio transmitter in wireless communication with a standard contraction recording device. However, other wireless communication devices can be used without deviating from the scope of the present invention.

It is well known to those skilled in the art that any number of light sources (30) can be used with the present invention. Such light sources (30) include light emitting diodes. For instance, an infrared laser diode is a suitable light source for use with the present invention. The present invention further includes a light detector (24a) responsive to changes in light beam emitted by the light source (30). Again, it is well known in the art that a wide variety of light detectors can be incorporated for use with the present invention. For example, the light detector (24a) can be a phototransistor, a photocell, a photosensitive diode or any other suitable light detector known in the art. Additionally, the signal decoder (24b) can include any of the various optical signal processing electronics known in the art. It should be understood, however, that in a broad sense the signal decoder (24b) is operable to convert into an appropriate output signal any change in the optical signal detected by the light detector (24a).

In a preferred embodiment, the signal transmitter (28) is a radio transmitter or other like wire less signal transmitter. Again, it is well known to those skilled in the art the extensive variety of radio transmitters that can be used in the present invention. In a preferred embodiment, the radio transmitter bandwidth is unique to the particular contraction recording device so as to prevent interference of the radio signal with other radio transmitting labor contraction devices (10) that may be in use. In this embodiment, the signal transmitter (28) can also provide communication with other monitoring equipment besides the contraction recording device. For instance, the transmitter (28) can be in communication with computer analysis equipment located at the nurses station or other remote location. It should also be understood that the transmitter (28) should provide a sufficient range of communication between the device (10) and the monitoring equipment to allow the mother to move freely about during the childbirth process. For example, a preferred transmitter (28) allows the mother to move outside the hospital room or about her own house during childbirth. Signal transmitters (28) providing the required range of communication distance are well known in the art.

Figure 3A:
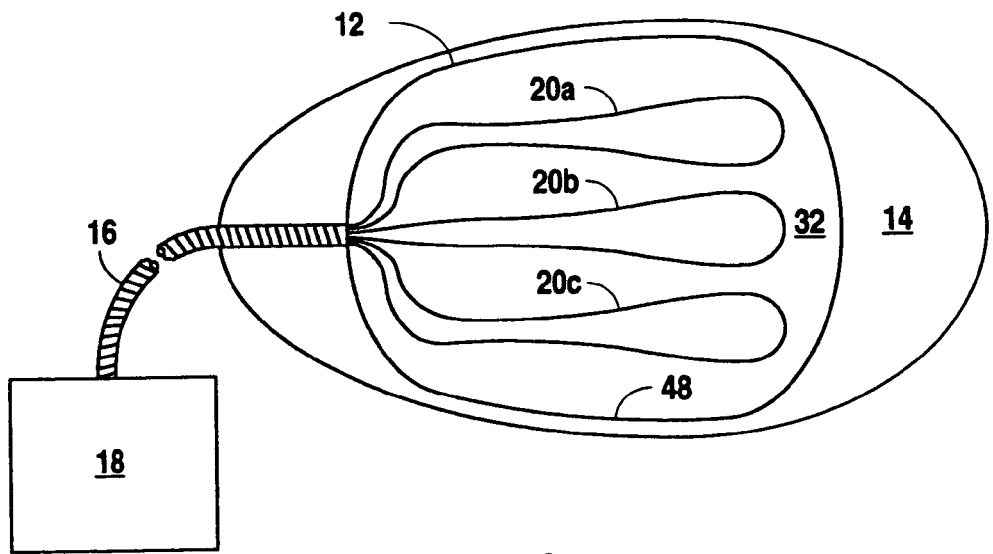

As illustrated by FIG. 3, the fiber optic strain sensor (12) comprises a single loop of fiber optic cable (20). When the cable (20) is not subject to external forces, the optical signal transmitted through the cable (20) is assigned a normal value. Upon the application of force, such as with a labor contraction, the cable (20) is distorted from its normal shape and a change in the optical signal of the light transmitted through the cable occurs. This change is detected by the light detector (24) and the signal is assigned a new value. It should therefore be understood that, as shown in FIG. 3A, the present invention covers within its scope the use of more than one fiber optic cable (20) to amplify any changes in the optical signal. More specifically, a fiber optic sensor (12) can be provided having multiple fiber optic cables (20a, 20b, and 20c) placed in parallel, wherein each individual cable (20) can be positioned at varying locations along the surface of the mother's abdomen. Additionally, more than one detector and/or light source can be utilized without deviating from the scope of the present invention.

It should be understood by those skilled in the art that power for the present invention can be provided by way of a standard power source (not shown). Importantly, the power source must be sufficient to provide continuous power to the device (10) for the entire period of labor. Suitable power sources generally include a battery pack comprising cadmium oxide or silver oxide batteries. It is clear, however, that the utilized batteries must be sized to allow packaging within the electronics box (18) or other placement so as to not limit patient mobility.

Various embodiments of the of the present invention have been described herein. It should be understood by those of ordinary skill in the art, however, that the above described embodiments of the present invention are set forth merely by way of example and should not be interpreted as limiting the scope of the present invention, which is defined by the appended claims. Many other alternative embodiments, variations and modifications of the foregoing embodiments that embrace various aspects of the present invention will also be understood upon a reading of the detailed description in light of the prior art. For instance, it will be understood that features of one embodiment may be combined with features of other embodiments while many other features may be omitted (or replaced) as being nonessential to the practice of the present invention.

What is claimed is:

1. A labor contraction sensing device comprising:
    a fiber optic strain sensor having an attachment surface adaptable for conforming said sensor to the contour of the abdomen of a pregnant female, wherein said attachment surface has a generally elliptical shape; and
    a signal transmitter in communication with said fiber optic strain sensor;
    said fiber optic strain sensor being operable for generating an output signal in response to a labor contraction of the pregnant female and communicating the output signal to said signal transmitter;
    said signal transmitter being operable for receiving the output signal and communicating the output signal to monitor the labor contraction.

2. A labor contraction sensing device comprising:
    a fiber optic strain sensor having an attachment surface adaptable for conforming said sensor to the contour of the abdomen of a pregnant female, wherein said attachment surface comprises a plurality of surface portions having a plurality of shapes for conforming to varying contours of the abdomen; and a signal transmitter in communication with said fiber optic strain sensor;

said fiber optic strain sensor being operable for generating an output signal in response to a labor contraction of the pregnant female and communicating the output signal to said signal transmitter; and said signal transmitter being operable for receiving the output signal and communicating the output signal to monitor the labor contraction.

3. A labor contraction sensing device comprising:

a fiber optic strain sensor having an attachment surface adaptable for conforming said sensor to the contour of the abdomen of a pregnant female, wherein said sensor has a generally elliptical shape; and a signal transmitter in communication with said fiber optic strain sensor;

said fiber optic strain sensor being operable for generating an output signal in response to a labor contraction of the pregnant female and communicating the output signal to said signal transmitter; and said signal transmitter being operable for receiving the output signal and communicating the output signal to monitor the labor contraction.

4. A labor contraction sensing device comprising:

a fiber optic strain sensor having an attachment surface adaptable for conforming said sensor to the contour of the abdomen of a pregnant female; and a signal transmitter in communication with said fiber optic strain sensor, wherein said sensor comprises a plurality of fiber optic cables;

said fiber optic strain sensor being operable for generating an output signal in response to a labor contraction of the pregnant female and communicating the output signal to said signal transmitter;

said signal transmitter being operable for receiving the output signal and communicating the output signal to monitor the labor contraction.

5. A labor contraction sensing device comprising:

a fiber optic strain sensor comprising a fiber optic cable disposed within a sensor cover;

said sensor cover having a surface conformable with the contour of the abdomen of a pregnant female;

an adhesive pad having a lower surface, an upper surface, and a compartment between said lower and upper surfaces;

said adhesive pad being adaptable for removably securing said sensor to the abdomen of the pregnant female; and an electronics box disposed within said compartment, said electronics box comprising a light source in communication with said cable, a light detector in communication with said cable, an optical signal processor in communication with said light detector, a signal transmitter in communication with said processor, and a power source connected to said light source, said light detector, said processor, and said transmitter;

wherein, in response to a labor contraction of the pregnant female, said sensor and said electronics box cooperate to generate and transmit an output signal representative of the labor contraction.

6. A labor contraction sensing device comprising:

an adhesive pad having a first surface and a second surface;

said first surface of said adhesive pad being removably attachable to and conformable to the contour of the abdomen of a pregnant female;

a fiber optic strain sensor attached to said second surface of said adhesive pad;

said fiber optic strain sensor comprising a fiber optic cable disposed within a sensor cover;

a light source in communication with said cable;

a light detector in communication with said cable;

an optical signal processor in communication with said light detector;

a signal transmitter in communication with said processor; and a power source connected to said light source, said light detector, said processor, and said transmitter;

wherein said light source, said light detector, said processor, said transmitter, and said power source are housed in an electronics box;

wherein said electronics box is disposed within a pouch adjacent to said sensor; and wherein, in response to a labor contraction of the pregnant female, said sensor, said light source, said light detector, said processor, and said transmitter cooperate to generate and transmit an output signal representative of the labor contraction.

* * * * *